(12) United States Patent
Ruchala et al.

(10) Patent No.: US 7,046,831 B2
(45) Date of Patent: *May 16, 2006

(54) SYSTEM AND METHOD FOR FUSION-ALIGNED REPROJECTION OF INCOMPLETE DATA

(75) Inventors: Kenneth J. Ruchala, Madison, WI (US); Gustavo H. Olivera, Verona, WI (US); Thomas R. Mackie, Verona, WI (US); Jeffrey M. Kapatoes, Madison, WI (US); Paul J. Reckwerdt, Madison, WI (US)

(73) Assignee: TomoTherapy Incorporated, Madison, WI (US)

( * ) Notice: Subject to any disclaimer, the term of this patent is extended or adjusted under 35 U.S.C. 154(b) by 338 days.

This patent is subject to a terminal disclaimer.

(21) Appl. No.: 09/802,468

(22) Filed: Mar. 9, 2001

(65) Prior Publication Data

US 2002/0136439 A1 Sep. 26, 2002

(51) Int. Cl.
*G06K 9/00* (2006.01)
*G06K 9/46* (2006.01)
*G06K 9/40* (2006.01)
*G06K 9/36* (2006.01)
*G06K 9/32* (2006.01)

(52) U.S. Cl. ............ 382/131; 382/132; 382/190; 382/275; 382/284; 382/294

(58) Field of Classification Search ............ 382/131, 382/151, 154; 250/363.04; 378/4, 21–27, 378/62, 63, 205, 407; 600/407
See application file for complete search history.

(56) References Cited

U.S. PATENT DOCUMENTS

| 5,317,616 | A |   | 5/1994  | Swerdloff et al. |
| 5,351,280 | A |   | 9/1994  | Swerdloff et al. |
| 5,394,452 | A |   | 2/1995  | Swerdloff et al. |
| 5,442,675 | A |   | 8/1995  | Swerdloff et al. |
| 5,528,650 | A |   | 6/1996  | Swerdloff et al. |
| 5,548,627 | A |   | 8/1996  | Swerdloff et al. |
| 5,552,605 | A | * | 9/1996  | Arata ............ 250/363.04 |
| 5,579,358 | A | * | 11/1996 | Lin ............... 378/4 |
| 5,625,190 | A | * | 4/1997  | Crandall ......... 250/363.03 |
| 5,625,663 | A |   | 4/1997  | Swerdloff et al. |
| 5,647,663 | A |   | 7/1997  | Holmes |
| 5,661,773 | A |   | 8/1997  | Swerdloff et al. |

(Continued)

OTHER PUBLICATIONS

Automatic registration of CT and MR brain images using correlation of geometrical features, Van den Elsen, P. et al.; Medical Imaging, IEEE Transactions on , vol.: 14, Jun. 1995.*

(Continued)

*Primary Examiner*—Samir Ahmed
(74) *Attorney, Agent, or Firm*—Michael Best & Friedrich LLP

(57) ABSTRACT

The present invention provides a system and method of using current but incomplete data to prepare an approximated complete image of a patient potentially undergoing radiation therapy. A limited patient image, such as that obtained from a CT scan is fused with a complete image of the same area using image registration techniques. The fused image is converted to sinogram data. This data is compared to sinogram data corresponding to the limited patient image to determine what data exists beyond the scope of the limited sinogram. Any additional data is added to the limited data sinogram to obtain a complete sinogram. This is reconstructed into an image that approximates the complete image that would have been taken at the time the limited image was obtained.

189 Claims, 3 Drawing Sheets

U.S. PATENT DOCUMENTS

| | | | |
|---|---|---|---|
| 5,673,300 | A | 9/1997 | Reckwerdt et al. |
| 5,724,400 | A | 3/1998 | Swerdloff et al. |
| 5,761,331 | A * | 6/1998 | Clark, III .................. 382/131 |
| 5,907,594 | A * | 5/1999 | Lai ............................. 378/4 |
| 5,963,664 | A * | 10/1999 | Kumar et al. ............... 382/154 |
| 6,266,453 | B1 * | 7/2001 | Hibbard et al. ............ 382/294 |
| 6,282,257 | B1 * | 8/2001 | Basu et al. .................. 378/15 |
| 6,324,243 | B1 * | 11/2001 | Edic et al. ..................... 378/4 |
| 6,915,005 | B1 * | 7/2005 | Ruchala et al. ............ 382/131 |

OTHER PUBLICATIONS

Kudo et al., Helical-scan Computed Tomography Using Cone-Beam Projections, IEEE Conference 1991, ISBN: 0-7803-0513, vol. 3, pp. 1958-1962.*

Website information; http://splweb.bwh.harvard.edu:8000/pages/papers/kikinis/hpc/hpcfinal.html; High Performance Computing (HPC) in Medical Image Analysis (MIA) at the Surgical Planning Laboratory (SPL); Ron Kikinis, M.D., Simon Warfield, Ph.D., Carl-Fredrik Westin, Ph.D.

Multimodality Image Registration By Maximization of Mutual Information; IEEE Transactions on Medical Imaging, vol. 16, No. 2, Apr. 1997; Frederik Maes, André Collignon, Dirk Vandermeulen, Guy Marchal, and Paul Suetens.

Multi-Modal Volume Registration by Maximization of Mutual Information; Medical Image Analysis, Oxford University Press; William M. Wells III; Paul Viola, Hideki Atsumi, Shin Nakajima, and Rod Kikinis.

Registration of Tomotheraphy Patients Using CT Projection Files; www.madrad.radiology.wisc.edu/tomo/registration/reg_iccr2/reg_iccr2.html; E.E.Fitchard, J.S. Aldridge, P.J. Reckwerdt, T.R. Mackie.

3D Treatment Planning and Intensity-Modulated Radiation Therapy; www.intouchlive.com/journals/oncology/o9910sup5s.htm; James A. Purdy, PhD.

Three-Dimensional Conformal Radiation Therapy (3DCRT) for Prostate Cancer; www.comed.com/Prostate/michalski; Jeff M. Michalski, MD, Carlos A. Perez, MD, and James A. Purdy, PhD.

Intensity Modulated Radiation Therapy: An Introduction for Patients and Clinicians; www.ocolink.upenn.edu/specialty/rad_onc/treat/imrt/imrt1.html; Jason Lee MD, Indra J. Das PhD, Shioa Y. Woo MD, Walter Grant PhD, Bin S. The MD, J. Kam Chiu MD, and E. Brian Butler MD.

* cited by examiner

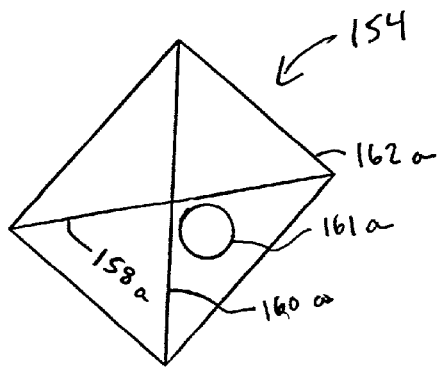
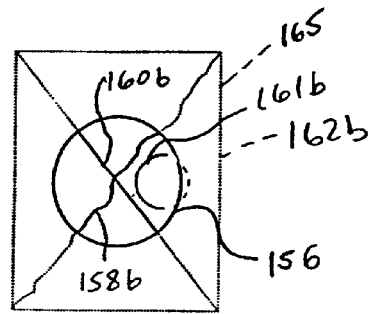
FIG. 5    FIG. 6
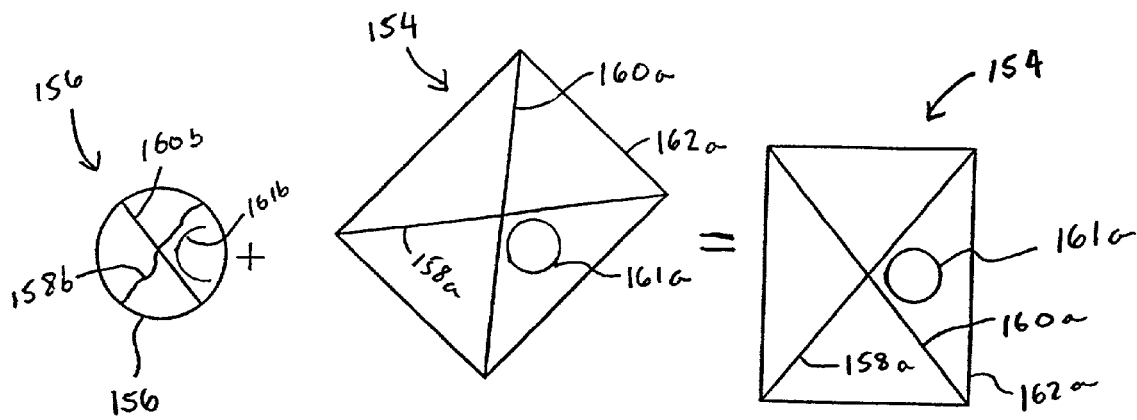
FIG. 7
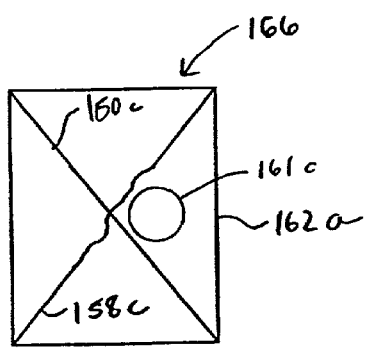
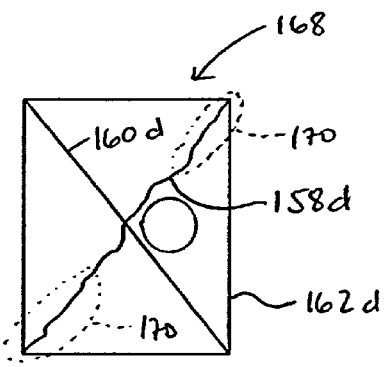
FIG. 8    FIG. 9

SYSTEM AND METHOD FOR FUSION-ALIGNED REPROJECTION OF INCOMPLETE DATA

FIELD OF THE INVENTION

This invention relates generally to radiation therapy and radiology, and more particularly to a method for reconstructing incomplete patient data for radiation therapy set-up and treatment verification.

BACKGROUND OF THE INVENTION

Medical equipment for radiation therapy treats tumorous tissue with high energy radiation. The amount of radiation and its placement must be accurately controlled to ensure both that the tumor receives sufficient radiation to be destroyed, and that the damage to the surrounding and adjacent non-tumorous tissue is minimized.

In external source radiation therapy, a radiation source external to the patient treats internal tumors. The external source is normally collimated to direct a beam only to the tumorous site. The source of high energy radiation may be x-rays, or electrons from linear accelerators in the range of 2–25 MeV, or gamma rays from highly focused radioisotopes such as a Co.sup.60 source having an energy of 1.25 MeV.

One form of external radiation therapy uses the precision of a computed tomography (CT) scanner to irradiate cancerous tissue because it acquires CT scans (e.g. megavoltage CT or kilo-voltage CT) immediately before, immediately after, or during radiation delivery, with the patient on a treatment apparatus and in the treatment position. This therapy technique uses intensity modulated beams that enter the patient's body at a greater number of angles and positions than conventional therapies, thereby lessening the amount of radiation that healthy tissues are subjected to and concentrating the radiation where it is needed most, at the cancer site(s). Essentially, the radiation field is "sculpted" to match the shape of the cancerous tissue to keep the dose of radiation to healthy tissue near the cancer low.

A radiation treatment plan may be based on a computed tomography ("CT") image of the patient. As is known in the art, a CT image is produced by a mathematical reconstruction of many projection images obtained at different angles about the patient. In a typical CT scan, the projections are one-dimensional line images indicating the attenuation of the beam by a "slice" of the patient. The actual CT data is held in a matrix wherein each row represents an angle and each column represents a distance. The matrix of data obtained in a CT scan can be displayed as a sinogram as shown in FIG. 1, or reconstructed into a two-dimensional image, as shown in FIG. 2.

In some radiotherapy systems, the oncologist views the cancerous areas on the CT image and determines the beam angles and intensities (identified with respect to the tumor image) which will be used to treat the tumor. In an automated system, such as that disclosed in U.S. Pat. No. 5,661,773, and hereby incorporated by reference, a computer program selects the beam angles and intensities after the physician identifies the tumorous region and upper and lower dose limits for the treatment.

More specifically, the planning images are used to create a 3-D treatment plan of a region of interest. This region of interest is broken down into units called voxels, which are defined as volumetric pixels. Each voxel is then assigned a particular radiation dose depending on what type of tissue or other matter it contains, e.g. cancerous tissue, air, etc.

Normally, the CT image of the patient is acquired substantially before the radiation treatment to allow time for the treatment plan to be prepared. However, the position of organs or other tissue to be treated can change from day-to-day because of a variety of factors. Further, patients move during treatment because of breathing, muscle twitching or the like. Uncertainty in the positioning of the patient with respect to the original CT image can undermine the conformality of the radiation delivery.

Thus, it is highly preferable to verify the treatment plan based on data obtained just prior to the time of treatment. The verification process can be done by techniques that compare the planning image to an image of the patient at the time of treatment.

Unfortunately, the data sets obtained on the day of treatment to be used for preparing the patient model are often incomplete. Patients that are large in size may not fit within the field-of-view (FOV) of the CT machine attached to the therapeutic equipment applying the radiation dose, and may yield an image such as that shown in FIG. 3, which shows only a portion of the image shown in FIG. 1. Not only is there a limited field of view, the data around the edges contains significant artifacts so that the image has an irregular white border and internal values are distorted. Alternatively, only a limited sample size of slices may have been obtained. There may be other limitations that result in the collection of incomplete data sets.

To resolve the problem of limited data sets in which only a portion of an image can be obtained, several scans of the patient may be made at various detector or patient positions, and then combined into a complete set. This has been done by adding together sinogram data, but requires that the imaging apparatus or patient position can be reliably modified accordingly, which is not always possible. Further, the problem of developing artifacts is still present due to the significant degree of mismatch between such data sets, and the additional handling of the patient is more costly, time intensive and can be difficult for frail patients. Moreover, the patients receive a higher dose of radiation with multiple scans than with one single scan.

Reconstruction of incomplete data sets using available techniques results in images that do not show the complete extent of the patient's body, can have artifacts and incorrect voxel values, and thus, limit the extent to which the images can be used for delivery verification, dose reconstruction and patient set-up, deformable patient registration and deformable dose registration. Accordingly, a need exists for a system and method that can solve the problems caused by limited data sets.

SUMMARY OF THE INVENTION

The present invention relates to a method by which an incomplete CT patient data set can be combined with an existing CT patient data set to create an image of a patient that is complete and without significant artifacts.

The method includes the steps of obtaining a first sinogram data set from a patient and a second sinogram data set or image from a patient. Both data sets are converted to images, and aligned together so that statistically, there is optimal registration between the two images. The aligned or "fused" image is reprojected as a sinogram. This reprojected sinogram is compared to either the first or second sinogram to determine what data exists beyond the scope of the first or second sinogram. This additional data is added to the sinogram to which the fused sinogram was compared to obtain an augmented sinogram The augmented sinogram is converted to an image, referred to as a fusion-aligned reprojection image.

The method of the present invention is advantageous in that the availability of only one limited data sinogram/image will not affect the ability to perform accurate delivery verification, dose reconstruction, patient set-up or the like. The limited data image or "first image" is fused to a previously taken complete image or "second image." The sinogram representing the fused image is compared to the limited data sinogram, and the augmented limited data sinogram is prepared therefrom. From the augmented limited data sinogram the fusion-aligned reprojected (FAR) image is obtained. The FAR image is used to accurately apply radiation to the treatment area, which may be positioned differently than as shown in the previously obtained complete image.

The advantages of obtaining current data at the time of treatment or even dosage verification are many. Damage to healthy tissue will be reduced, and the cancerous or diseased tissue will be more accurately targeted. These differences are especially critical in areas that have frequent internal anatomy changes, such as the torso or prostate.

While the present invention is particularly useful in the medical field, other applications are possible and references to use in cancer therapy should not be deemed to limit the application of the present invention. The present invention may be advantageously adapted for use where similar performance capabilities and characteristics are desired. These and other objects and advantages of the present invention will become apparent from the detailed description, claims, and accompanying drawings.

BRIEF DESCRIPTION OF THE DRAWINGS

FIG. 5 is a schematic example of a patient CT scan;

FIG. 6 is a limited schematic view of FIG. 6, showing the limited scan portion in the center of the object, and the remaining nonscanned portion in phantom;

FIG. 7 demonstrates how the limited image of FIG. 6 is aligned with the full image of FIG. 5 through the process of fusion;

FIG. 8 is a schematic view of a fusion aligned reprojection image;

FIG. 9 is a schematic view of a full image corresponding to that in FIG. 6;

DETAILED DESCRIPTION

Figure 4:
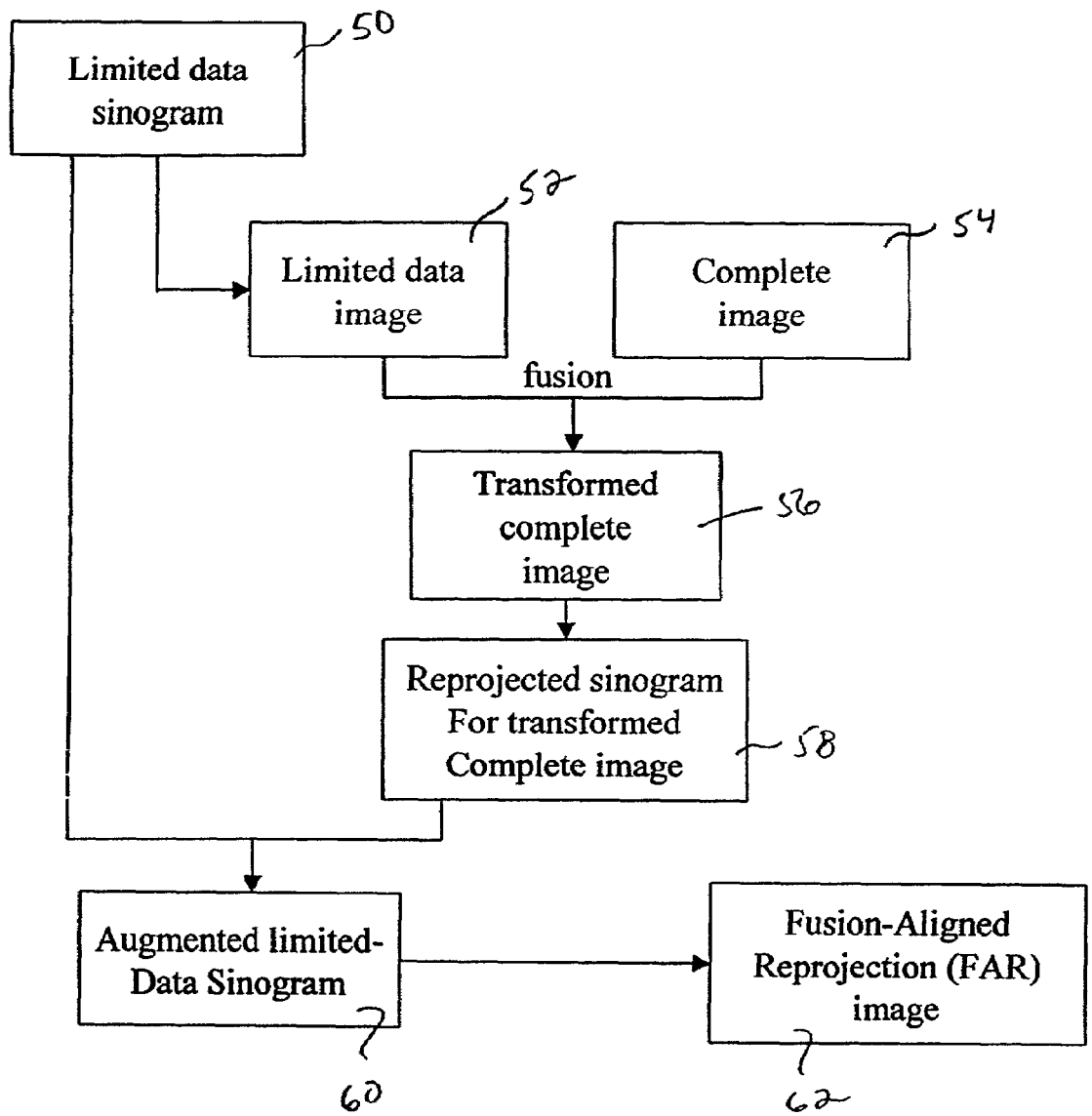
FIG. 4 is a flowchart showing the process steps of the present invention.

A preferred method in accordance with the present invention is shown in the flowchart of FIG. 4. A limited data sinogram 50 representing the treatment area is obtained from a patient. In one preferred embodiment of the present invention, the limited data sinogram 50 is prepared near the time that the patient is receiving his or her radiation treatment. However, the limited data sinogram 50 may be obtained at any time.

Figure 3:
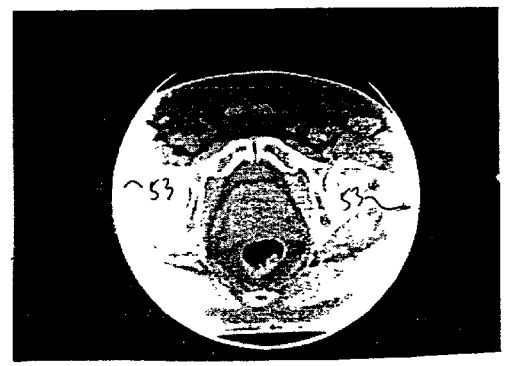
FIG. 3 is an example CT image with a limited field of view.

The limited data sinogram 50 is reconstructed to a limited data image 52, as seen in the example of FIG. 3, and represented schematically in FIG. 6 as limited object 156. FIG. 3 contains a significant amount of artifacts such as the white irregular border 53, and some distortion of image values. By way of example, the treatment area targeted in FIG. 3 is a prostate gland. The method can be applied to images of any part of the body, or be used in veterinary or radiological applications.

Figure 2:
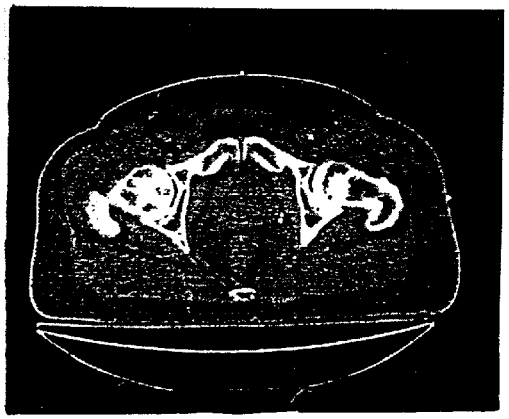
FIG. 2 is an example of a planning CT image obtained from a CT-scan sinogram similar to that shown in FIG. 1.

A complete image 54 of the same patient and same treatment area is seen in FIG. 2, and represented schematically in FIG. 5 as object 154. Typically, this complete image 54 will have been made prior to obtaining the limited data image 52 for the purpose of treatment planning. Even if limited image 52 were taken only minutes after the complete data image 54, there are almost always inherent differences between the location of certain organs or tissue due to patient motion or other bodily functions. If enough time has elapsed between images, weight loss or growth of certain tissue can occur.

It is noted that complete image 54 or limited image 52 need not be from CT scans, and that this technique can be generally applied to matching images from different projection imaging modalities such as magnetic resonance imaging, positron emission tomography, and single photon emission tomography. Thus, there may be misalignment or disagreement between the two images because of differing methods of data collection.

The two images shown in FIGS. 2 and 3 and represented schematically by objects 154 and 156, in FIGS. 5 and 6 have differences between them. In the actual image example of FIGS. 2 and 3, intestinal gas is shown in FIG. 3, thereby displacing the treatment target. In the schematic example, object 154 is composed of diagonals 158a and 160a and an inclusion 161a, within a frame 162a. Limited object 156 shows only corresponding diagonals 160b and 158b, and part of the inclusion designated as 161b. Thus, there is a change between diagonal 158a and 158b and only partial data for inclusion 161b.

Figure 1:
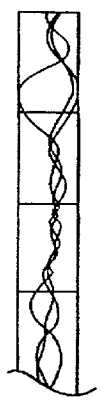
FIG. 1 an example of a sinogram obtained from the CT scan of a patient.
Figure 7A:
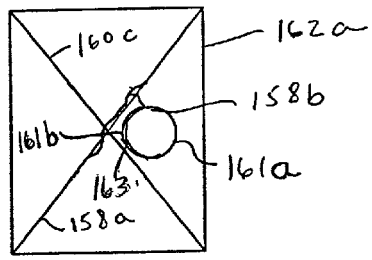
FIG. 7A show the actual alignment or "fusion" of the images from FIGS. 5 and 6.

Referring to FIG. 7, "fusion" or image registration techniques are used to align limited data image 52 with complete image 54. In the schematic example, limited object 156 is fused with complete object 154 so that statistically, there is optimal registration between the objects 154 and 156. FIG. 7 shows how the orientation of object 154 is aligned to closely match that of object 156. FIG. 7A shows diagonal 160c as the perfect registration between diagonals 160a and 160b. There is less than perfect registration between diagonals 158a and 158b. Both lines are superimposed only by way of example to show that fusion is not perfect as evidenced by the double edge 163.

Image registration or fusion may be achieved by several techniques. One such technique is known as mutual information (MI), for which a well-known algorithm has been developed. One such example of this algorithm being used to register multi-modal images is described in the following publication, incorporated herein by reference: Frederik Maes, Andre Collignon, Dirk Vendermeulen, Guy Marchal, and Paul Suetens, *Multimodality Image Registration by Maximization of Mutual Information*, Vol. 16, No. 2, IEEE Transactions on Medical Imaging, 187 (April 1997).

Extracted Feature Fusion (EFF) is another registration technique providing numerous advantages over prior art techniques. EFF is a voxel-based image registration method, wherein only extracted features of images are registered or fused. For example, a patient's bone structure usually stays the same even when a patient loses a substantial amount of weight. Therefore, the bones can in effect be extracted from each image subject to alignment, and then registered using statistical methods. In the simple example of FIG. 5, diagonal 160a and frame 162 may represent bone or tissue that remains relatively unchanged over time. Therefore, only these relatively static features might be selected for fusion, while other features that are more dynamic, perhaps diagonals 158a,b and inclusion 161a,b, need not be included in the registration calculations.

The benefits of registering only an extracted portion of an image are reduced calculation times, improved accuracy, and more clearly defined goals for alignment in cases where the patient has significantly changed in shape. The benefits arise from the registration of fewer data points, which in this case are voxels. The total processing time is generally proportional to the number of points selected, so reducing that number from the size of the entire three-dimensional image set to a subset of points meeting certain criteria (e.g. voxels that represent bone or do not represent air) will typically reduce calculation times. This reduction of voxels can provide more accurate results than other methods of reducing the number of voxels for MI techniques, such as regular down-sampling.

Other image registration techniques include manual fusion, alignment using geometric features (e.g. surfaces), gradient methods, and voxel-similarity techniques.

Referring back to FIG. 4, the aligned or transformed complete image 56 is reprojected as a sinogram 58. The data for sinogram 58 is once again in a matrix wherein each row represents an angle, and each column represents distance. The data matrix of the reprojected sinogram is compared to the data matrix for limited data sinogram 50 to determine what data is missing from the limited sinogram. This is now possible because the complete sinogram is in alignment with the limited sinogram.

Figure 10:
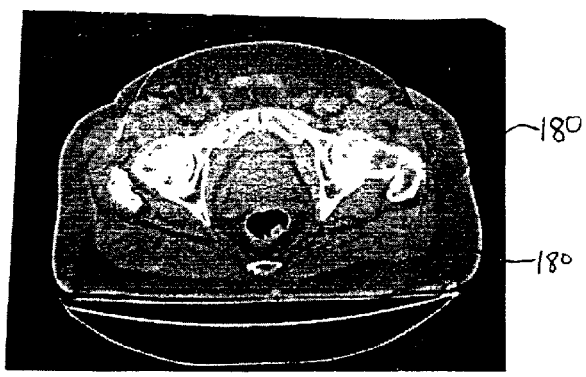
FIG. 10 is a reconstructed image of FIGS. 2 and 3 fused and aligned in accordance with the method of the present invention.

The approximation of the missing sinogram data from the reprojected, fusion aligned version of image 154 is added to the limited sinogram 50 to create an augmented limited data sinogram, or augmented sinogram 60. The augmented sinogram 60 is reconstructed to a fusion aligned reprojection image (FAR image) 62 that is an approximation of what the complete image would have looked like at the time the limited data image was obtained. The FAR image 62 is represented schematically in FIG. 8. Frame 162 is the same as in FIG. 5, and diagonals 158c, 160c and inclusion 161c are now complete. This can compared to the object 168 in FIG. 9, which represents the image that would have been taken at the time of treatment if it were possible to obtain a complete image. The fact that the outer regions 170 of diagonal 158d are not the same as diagonal 158c is not critical to the invention. FIG. 10 represents a reconstructed image obtained by combining FIGS. 2 and 3 in accordance with the method of the present invention. It can be seen that slight artifacts such as the faint ring 180 can result. However, such artifacts are insignificant because they do not impair the conspicuity of the important structures in the field of view, nor do they noticeably detriment dose calculations or other processes that utilize these images.

The reconstructed image obtained from method of the present invention can then be used for patient setup (positioning the patient prior to delivery), dose registration (changing delivery patterns to compensate for patient position or tumor shape changes), delivery verification (using a signal measured at an exit detector to compute energy fluence directed toward a patient), deformable patient registration and deformable dose registration (using anatomical, biomechanical and region of interest data to map changes in the patient's anatomy between each fraction, a reconstructed dose is mapped to a reference image to obtain a cumulative dose).

It will be understood to those of ordinary skill in the art that other methods of comparing images may be used including, for example, those which would recognize changes beyond rigid body translation or rotation.

Although the invention has been herein shown and described in what is perceived to be the most practical and preferred embodiments, it is to be understood that the invention is not intended to be limited to the specific embodiments set forth above. It is recognized that modifications may be made by one of skill in the art of the invention without departing from the spirit or intent of the invention and therefore, the invention is to be taken as including all reasonable equivalents to the subject matter of the appended claims.

We claim:

1. A method of augmenting a tomographic projection image of a patient, the method comprising the steps of:

obtaining a first sinogram data set from a patient, the first sinogram data set including incomplete or imperfect data;

reconstructing the first sinogram data set into a first image;

aligning the first image to a second image, the second image being separate and independent from the first image and obtained from the patient at a different time from the first image, the second image including complete image data to obtain an aligned image, so that optimal registration between the first and second image is obtained;

reprojecting the aligned image into a reprojected sinogram data set;

extracting data from the reprojected sinogram data set that is missing from or not available in the first sinogram data set;

augmenting the first sinogram data set with the extracted data from the reprojected sinogram data set to obtain an augmented sinogram data set; and reconstructing the augmented sinogram data set into a third image.

2. A method of augmenting a tomographic projection image of a patient, the method comprising the steps of:

converting a first limited data sinogram obtained from a patient to a first limited image, the first limited data sinogram and the first limited image including incomplete or imperfect data;

fusing the first limited image to a second complete image, the second complete image being separate and independent from the first image and obtained from the patient at a different time from the first limited image, the second complete image including complete image data to obtain a transformed complete image;

reprojecting a sinogram data set from the transformed complete image to obtain a reprojected complete data sinogram;

extracting data from the reprojected complete data sinogram that is missing from or not available in the first limited data sinogram;

augmenting the first limited data sinogram with the extracted data from the reprojected complete data sinogram to obtain an augmented limited data sinogram; and converting the augmented limited data sinogram into an augmented image.

3. The method according to claim 2 wherein the step of fusing comprises the steps of extracting certain features from the first limited image and the second complete image and registering the features into the transformed complete image.

4. The method according to claim 2 wherein the step of fusing is performed manually.

5. The method according to claim 2 wherein the step of fusing is performed automatically.

6. The method according to claim 2 wherein the step of fusing is performed using geometric features, gradient methods or voxel-similarity techniques.

7. The method according to claim 2 wherein the first limited data sinogram, the reprojected complete data sinogram and the augmented data sinogram is represented by a data matrix wherein each row represents an angle and each column represents a distance.

8. The method according to claim 6 further comprising the steps of comparing the data matrix of the reprojected complete data sinogram to the data matrix for the first limited data sinogram and determining what data is missing from the first limited data sinogram.

9. The method according to claim 2 further comprising the steps of using the augmented image any of the following: contouring, patient setup, patient repositioning, dose registration, dose calculation, dose patching, dose reconstruction, dose verification, delivery modification, plan selection, replanning, re-optimization, delivery verification, deformable patient registration, and deformable dose registration.

10. The method according to claim 1 wherein the step of aligning comprises the steps of extracting certain features from the first image and the second image and registering the features.

11. The method according to claim 1 wherein the step of aligning comprises using common radiotherapy patient setup protocols.

12. The method according to claim 1 wherein the first sinogram data set, the reprojected sinogram data set and the augmented sinogram data set are represented by a data matrix wherein each row represents an angle and each column represents distance.

13. The method according to claim 1 further comprising the steps of using the augmented image for any of the following: contouring, patient setup, patient repositioning, dose registration, dose calculation, dose patching, dose reconstruction, dose verification, delivery modification, plan selection, replanning, re-optimization, delivery verification, deformable patient registration, and deformable dose registration.

14. A method of reconstructing a limited data image from a complete data image, the method comprising the steps of:

obtaining a first sinogram data set from a patient, the first sinogram data set including incomplete, imperfect or limited data;

reconstructing the first sinogram data set into a first image;

obtaining a second sinogram data set from the patient at a different time from the first sinogram data set, the second sinogram data set including more complete data than the first sinogram data set;

reconstructing the second sinogram data set into a second image;

fusing the first image to the second image;

aligning the second image to the first image to obtain an aligned image;

reprojecting the aligned image into a reprojected sinogram data set;

extracting data from the reprojected sinogram data set that is missing from or not available in the first sinogram data set;

augmenting the first sinogram data set with the extracted data from the reprojected sinogram data set to obtain an augmented sinogram data set; and reconstructing the augmented sinogram data set into a fusion-aligned reprojection image.

15. The method according to claim 14 wherein the second sinogram data set includes limited data, but is less-limited or limited in a different manner than the first sinogram data set such that the first sinogram data set can be augmented from the second sinogram data set or the reprojected sinogram data set.

16. The method according to claim 14 wherein the first image is realigned to the second image to obtain an aligned image, the aligned image is reprojected into a reprojected sinogram data set, and data is extracted from the reprojected sinogram data set to augment data into the first or second sinogram data set to obtain an augmented sinogram data set.

17. A method of augmenting a tomographic projection image of a patient, the method comprising the steps of:

obtaining a first sinogram data set from a patient, the first sinogram data set including incomplete, imperfect or limited data;

obtaining a second sinogram data set from the patient at a different time from the first sinogram data set, the second sinogram data set including complete data;

aligning the first sinogram data set to the second sinogram data set to obtain an aligned sinogram data set, so that optimal registration between the first and second sinogram data sets is obtained;

extracting data from the aligned sinogram data set that is missing from or not available in the first sinogram data set;

augmenting the first sinogram data set with the extracted data from the aligned sinogram data set to obtain an augmented sinogram data set; and reconstructing the augmented sinogram data set into a fusion-aligned reprojection image.

18. The method according to claim 1 wherein the first sinogram data set is converted to an artifact-prone image.

19. The method according to claim 1 wherein the step of aligning comprises using common radiotherapy patient setup protocols.

20. The method according to claim 1 wherein the first and second images are sufficiently well aligned that explicit fusion is not necessary.

21. The method according to claim 1 wherein the first sinogram data set, the reprojected sinogram data set and the augmented sinogram data set are represented by a data matrix wherein each row represents a gantry position, a gantry angle, or a ray angle; and each column represents a detector number, a detector distance, a detector angle, or a ray position; and a third sinogram dimension may optionally represent multiple detector rows.

22. The method according to claim 1 wherein the first sinogram data set is obtained from megavoltage CT images and the second image is obtained from kilovoltage CT images.

23. The method according to claim 1 wherein the first sinogram data set is obtained from kilovoltage CT images and the second image is obtained from megavoltage CT images.

24. The method according to claim 1 wherein the first sinogram data set is obtained from CT images and the second image is obtained from MRI images.

25. The method according to claim 1 wherein the first sinogram data set is obtained from MRI images and the second image is obtained from CT images.

26. The method according to claim 1 wherein the first sinogram data set is obtained from CT images and the second image is obtained from PET images.

27. The method according to claim 1 wherein the first sinogram data set is obtained from PET images and the second image is obtained from CT images.

28. The method according to claim 1 wherein the first sinogram data set is obtained from MRI images and the second image is obtained from PET images.

29. The method according to claim 1 wherein the first sinogram data set is obtained from PET images and the second image is obtained from MRI images.

30. The method according to claim 1 further comprising the step of completing one or more iterations by substituting the third image for the first image.

31. The method according to claim 1 wherein the first sinogram data set is obtained from a tomographic or volume-imaging modality.

32. The method according to claim 1 wherein the second image is obtained from a tomographic or volume-imaging modality.

33. The method according to claim 1 wherein any of the sinograms or images are collected using fan-beam geometries.

34. The method according to claim 1 wherein any of the sinograms or images are collected using cone-beam geometries.

35. The method according to claim 1 wherein any of the sinograms or images are collected using helical geometries.

36. The method according to claim 1 wherein any of the sinograms or images are collected using planar image or data converted into tomographic-equivalent images or sinograms, or volume images.

37. The method according to claim 1 wherein the steps of extracting data and/or augmenting data utilizes patient shape, size, or density information.

38. The method according to claim 1 wherein the patient's size, shape, and/or anatomy has changed between the collection of the first and second images or data sets.

39. The method according to claim 2 wherein the first limited data sinogram is converted to an artifact-prone image.

40. The method according to claim 2 wherein the step of fusing comprises using common radiotherapy patient setup protocols.

41. The method according to claim 2 wherein the first limited image and the second complete image are sufficiently well aligned that explicit fusion is not necessary.

42. The method according to claim 2 wherein the first limited data sinogram, the reprojected complete data sinogram and the augmented limited data sinogram are represented by a data matrix wherein each row represents a gantry position, a gantry angle, or a ray angle; and each column represents a detector number, a detector distance, a detector angle, or a ray position; and a third sinogram dimension may optionally represent multiple detector rows.

43. The method according to claim 2 wherein the first limited data sinogram is obtained from megavoltage CT images and the second complete image is obtained from kilovoltage CT images.

44. The method according to claim 2 wherein the first limited data sinogram is obtained from kilovoltage CT images and the second complete image is obtained from megavoltage CT images.

45. The method according to claim 2 wherein the first limited data sinogram is obtained from CT images and the second complete image is obtained from MRI images.

46. The method according to claim 2 wherein the first limited data sinogram is obtained from MRI images and the second complete image is obtained from CT images.

47. The method according to claim 2 wherein the first limited data sinogram is obtained from CT images and the second complete image is obtained from PET images.

48. The method according to claim 2 wherein the first limited data sinogram is obtained from PET images and the second complete image is obtained from CT images.

49. The method according to claim 2 wherein the first limited data sinogram is obtained from MRI images and the second complete image is obtained from PET images.

50. The method according to claim 2 wherein the first limited data sinogram is obtained from PET images and the second complete image is obtained from MRI images.

51. The method according to claim 2 further comprising the step of completing one or more iterations by substituting the augmented image for the first limited image.

52. The method according to claim 2 wherein the first limited data sinogram is obtained from a tomographic or volume-imaging modality.

53. The method according to claim 2 wherein the second complete image is obtained from a tomographic or volume-imaging modality.

54. The method according to claim 2 wherein any of the sinograms or images are collected using fan-beam geometries.

55. The method according to claim 2 wherein any of the sinograms or images are collected using cone-beam geometries.

56. The method according to claim 2 wherein any of the sinograms or images are collected using helical geometries.

57. The method according to claim 2 wherein any of the sinograms or images are collected using planar image or data converted into tomographic-equivalent images or sinograms, or volume images.

58. The method according to claim 2 wherein the step of augmenting data utilizes patient shape, size, or density information.

59. The method according to claim 2 wherein the patient's size, shape, and/or anatomy has changed between the collection of the first and second images or data sets.

60. The method according to claim 14 wherein the first sinogram data set is converted to an artifact-prone image.

61. The method according to claim 14 wherein the step of fusing comprises using common radiotherapy patient setup protocols.

62. The method according to claim 14 wherein the first and second images are sufficiently well aligned that explicit fusion is not necessary.

63. The method according to claim 14 wherein the first sinogram data set, the reprojected sinogram data set and the augmented sinogram data set are represented by a data matrix wherein each row represents a gantry position, a gantry angle, or a ray angle; and each column represents a detector number, a detector distance, a detector angle, or a ray position; and a third sinogram dimension may optionally represent multiple detector rows.

64. The method according to claim 14 wherein the first sinogram data set is obtained from megavoltage CT images and the second sinogram data set is obtained from kilovoltage CT images.

65. The method according to claim 14 wherein the first sinogram data set is obtained from kilovoltage CT images and the second sinogram data set is obtained from megavoltage CT images.

66. The method according to claim 14 wherein the first sinogram data set is obtained from CT images and the second sinogram data set is obtained from MRI images.

67. The method according to claim 14 wherein the first sinogram data set is obtained from MRI images and the second sinogram data set is obtained from CT images.

68. The method according to claim 14 wherein the first sinogram data set is obtained from CT images and the second sinogram data set is obtained from PET images.

69. The method according to claim 14 wherein the first sinogram data set is obtained from PET images and the second sinogram data set is obtained from CT images.

70. The method according to claim 14 wherein the first sinogram data set is obtained from MRI images and the second sinogram data set is obtained from PET images.

71. The method according to claim 14 wherein the first sinogram data set is obtained from PET images and the second sinogram data set is obtained from MRI images.

72. The method according to claim 14 further comprising the step of completing one or more iterations by substituting the fusion-aligned reprojection image for the first image.

73. The method according to claim 14 wherein the first sinogram data set is obtained from a tomographic or volume-imaging modality.

74. The method according to claim 14 wherein the second sinogram data set is obtained from a tomographic or volume-imaging modality.

75. The method according to claim 14 wherein any of the sinograms or images are collected using fan-beam geometries.

76. The method according to claim 14 wherein any of the sinograms or images are collected using cone-beam geometries.

77. The method according to claim 14 wherein any of the sinograms or images are collected using helical geometries.

78. The method according to claim 14 wherein any of the sinograms or images are collected using planar image or data converted into tomographic-equivalent images or sinograms, or volume images.

79. The method according to claim 14 wherein the step of merging utilizes patient shape, size, or density information.

80. The method according to claim 14 wherein the patient's size, shape, and/or anatomy has changed between the collection of the first and second images or data sets.

81. The method according to claim 17 wherein the first sinogram data set is converted to an artifact-prone image.

82. The method according to claim 17 wherein the step of fusing comprises using common radiotherapy patient setup protocols.

83. The method according to claim 17 wherein the sinogram data sets are sufficiently well aligned that explicit fusion is not necessary.

84. The method according to claim 17 wherein the first sinogram data set, the aligned sinogram data set and the augmented sinogram data set are represented by a data matrix wherein each row represents a gantry position, a gantry angle, or a ray angle; and each column represents a detector number, a detector distance, a detector angle, or a ray position; and a third sinogram dimension may optionally represent multiple detector rows.

85. The method according to claim 17 wherein the first sinogram data set is obtained from megavoltage CT images and the second sinogram data set is obtained from kilovoltage CT images.

86. The method according to claim 17 wherein the first sinogram data set is obtained from kilovoltage CT images and the second sinogram data set is obtained from megavoltage CT images.

87. The method according to claim 17 wherein the first sinogram data set is obtained from CT images and the second sinogram data set is obtained from MRI images.

88. The method according to claim 17 wherein the first sinogram data set is obtained from MRI images and the second sinogram data set is obtained from CT images.

89. The method according to claim 17 wherein the first sinogram data set is obtained from CT images and the second sinogram data set is obtained from PET images.

90. The method according to claim 17 wherein the first sinogram data set is obtained from PET images and the second sinogram data set is obtained from CT images.

91. The method according to claim 17 wherein the first sinogram data set is obtained from MRI images and the second sinogram data set is obtained from PET images.

92. The method according to claim 17 wherein the first sinogram data set is obtained from PET images and the second sinogram data set is obtained from MRI images.

93. The method according to claim 17 further comprising the step of completing one or more iterations by substituting the augmented sinogram data set for the first sinogram data set.

94. The method according to claim 17 wherein the first sinogram data set is obtained from a tomographic or volume-imaging modality.

95. The method according to claim 17 wherein the second sinogram data set is obtained from a tomographic or volume-imaging modality.

96. The method according to claim 17 wherein any of the sinograms or images are collected using fan-beam geometries.

97. The method according to claim 17 wherein any of the sinograms or images are collected using cone-beam geometries.

98. The method according to claim 17 wherein any of the sinograms or images are collected using helical geometries.

99. The method according to claim 17 wherein any of the sinograms or images are collected using planar image or data converted into tomographic-equivalent images or sinograms, or volume images.

100. The method according to claim 17 wherein the step of merging utilizes patient shape, size, or density information.

101. The method according to claim 17 wherein the patient's size, shape, and/or anatomy has changed between the collection of the first and second data sets.

102. A method of augmenting a tomographic projection image of a patient, the method comprising the steps of:
   obtaining a first sinogram data set from a patient, the first sinogram data set including incomplete or imperfect data;
   reconstructing the first sinogram data set into a first image;
   aligning the first image to a second image, the second image being separate and independent from the first image and obtained from the patient using a different imaging apparatus or modality than the first image, the second image including complete image data to obtain an aligned image, so that optimal registration between the first and second image is obtained;

reprojecting the aligned image into a reprojected sinogram data set;

extracting data from the reprojected sinogram data set that is missing from or not available in the first sinogram data set;

augmenting the first sinogram data set with the extracted data from the reprojected sinogram data set to obtain an augmented sinogram data set; and reconstructing the augmented sinogram data set into a third image.

103. The method according to claim 102 wherein the first sinogram data set is converted to an artifact-prone image.

104. The method according to claim 102 wherein the step of aligning comprises using common radiotherapy patient setup protocols.

105. The method according to claim 102 wherein the first and second images are sufficiently well aligned that explicit fusion is not necessary.

106. The method according to claim 102 wherein the first sinogram data set, the reprojected sinogram data set and the augmented sinogram data set are represented by a data matrix wherein each row represents a gantry position, a gantry angle, or a ray angle; and each column represents a detector number, a detector distance, a detector angle, or a ray position; and a third sinogram dimension may optionally represent multiple detector rows.

107. The method according to claim 102 wherein the first sinogram data set is obtained from megavoltage CT images and the second image is obtained from kilovoltage CT images.

108. The method according to claim 102 wherein the first sinogram data set is obtained from kilovoltage CT images and the second image is obtained from megavoltage CT images.

109. The method according to claim 102 wherein the first sinogram data set is obtained from CT images and the second image is obtained from MRI images.

110. The method according to claim 102 wherein the first sinogram data set is obtained from MRI images and the second image is obtained from CT images.

111. The method according to claim 102 wherein the first sinogram data set is obtained from CT images and the second image is obtained from PET images.

112. The method according to claim 102 wherein the first sinogram data set is obtained from PET images and the second image is obtained from CT images.

113. The method according to claim 102 wherein the first sinogram data set is obtained from MRI images and the second image is obtained from PET images.

114. The method according to claim 102 wherein the first sinogram data set is obtained from PET images and the second image is obtained from MRI images.

115. The method according to claim 102 further comprising the step of completing one or more iterations by substituting the third image for the first image.

116. The method according to claim 102 wherein the first sinogram data set is obtained from a tomographic or volume-imaging modality.

117. The method according to claim 102 wherein the second image is obtained from a tomographic or volume-imaging modality.

118. The method according to claim 102 wherein any of the sinograms or images are collected using fan-beam geometries.

119. The method according to claim 102 wherein any of the sinograms or images are collected using cone-beam geometries.

120. The method according to claim 102 wherein any of the sinograms or images are collected using helical geometries.

121. The method according to claim 102 wherein any of the sinograms or images are collected using planar image or data converted into tomographic-equivalent images or sinograms, or volume images.

122. The method according to claim 102 wherein the steps of extracting data and/or augmenting data utilizes patient shape, size, or density information.

123. The method according to claim 102 wherein the patient's size, shape, and/or anatomy has changed between the collection of the first and second images or data sets.

124. A method of augmenting a tomographic projection image of a patient, the method comprising the steps of:

converting a first limited data sinogram obtained from a patient to a first limited images, the first limited data sinogram and the first limited image including incomplete or imperfect data;

fusing the first limited image to a second complete image, the second complete image being separate and independent from the first image and obtained from the patient using a different imaging apparatus or modality than the first limited image, the second complete image including complete image data to obtain a transformed complete image;

reprojecting a sinogram data set from the transformed complete image to obtain a reprojected complete data sinogram;

extracting data from the reprojected complete data sinogram that is missing from or not available in the first limited data sinogram;

augmenting the first limited data sinogram with the extracted data from the reprojected complete data sinogram to obtain an augmented limited data sinogram; and converting the augmented limited data sinogram into an augmented image.

125. The method according to claim 124 wherein the first limited data sinogram is converted to an artifact-prone image.

126. The method according to claim 124 wherein the step of fusing comprises using common radiotherapy patient setup protocols.

127. The method according to claim 124 wherein the first limited image and the second complete image are sufficiently well aligned that explicit fusion is not necessary.

128. The method according to claim 124 wherein the first limited data sinogram, the reprojected complete data sinogram and the augmented limited data sinogram are represented by a data matrix wherein each row represents a gantry position, a gantry angle, or a ray angle; and each column represents a detector number, a detector distance, a detector angle, or a ray position; and a third sinogram dimension may optionally represent multiple detector rows.

129. The method according to claim 124 wherein the first limited data sinogram is obtained from megavoltage CT images and the second complete image is obtained from kilovoltage CT images.

130. The method according to claim 124 wherein the first limited data sinogram is obtained from kilovoltage CT images and the second complete image is obtained from megavoltage CT images.

131. The method according to claim 124 wherein the first limited data sinogram is obtained from CT images and the second complete image is obtained from MRI images.

132. The method according to claim 124 wherein the first limited data sinogram is obtained from MRI images and the second complete image is obtained from CT images.

133. The method according to claim 124 wherein the first limited data sinogram is obtained from CT images and the second complete image is obtained from PET images.

134. The method according to claim 124 wherein the first limited data sinogram is obtained from PET images and the second complete image is obtained from CT images.

135. The method according to claim 124 wherein the first limited data sinogram is obtained from MRI images and the second complete image is obtained from PET images.

136. The method according to claim 124 wherein the first limited data sinogram is obtained from PET images and the second complete image is obtained from MRI images.

137. The method according to claim 124 further comprising the step of completing one or more iterations by substituting the augmented image for the first limited image.

138. The method according to claim 124 wherein the first limited data sinogram is obtained from a tomographic or volume-imaging modality.

139. The method according to claim 124 wherein the second complete image is obtained from a tomographic or volume-imaging modality.

140. The method according to claim 124 wherein any of the sinograms or images are collected using fan-beam geometries.

141. The method according to claim 124 wherein any of the sinograms or images are collected using cone-beam geometries.

142. The method according to claim 124 wherein any of the sinograms or images are collected using helical geometries.

143. The method according to claim 124 wherein any of the sinograms or images are collected using planar image or data converted into tomographic-equivalent images or sinograms, or volume images.

144. The method according to claim 124 wherein the step of augmenting data utilizes patient shape, size, or density information.

145. The method according to claim 124 wherein the patient's size, shape, and/or anatomy has changed between the collection of the first and second images or data sets.

146. A method of reconstructing a limited data image from a complete data image, the method comprising the steps of:
obtaining a first sinogram data set from a patient, the first sinogram data set including incomplete, imperfect or limited data;
reconstructing the first sinogram data set into a first image;
obtaining a second sinogram data set from the patient using a different imaging apparatus or modality than the first sinogram data set, the second sinogram data set including more complete data than the first sinogram data set;
reconstructing the second sinogram data set into a second image;
fusing the first image to the second image;
aligning the second image to the first image to obtain an aligned image;
reprojecting the aligned image into a reprojected sinogram data set;
extracting data from the reprojected sinogram data set that is missing from or not available in the first sinogram data set;
augmenting the first sinogram data set with the extracted data from the reprojected sinogram data set to obtain an augmented sinogram data set; and
reconstructing the augmented sinogram data set into a fusion-aligned reprojection image.

147. The method according to claim 146 wherein the first sinogram data set is converted to an artifact-prone image.

148. The method according to claim 146 wherein the step of fusing comprises using common radiotherapy patient setup protocols.

149. The method according to claim 146 wherein the first and second images are sufficiently well aligned that explicit fusion is not necessary.

150. The method according to claim 146 wherein the first sinogram data set, the reprojected sinogram data set and the augmented sinogram data set are represented by a data matrix wherein each row represents a gantry position, a gantry angle, or a ray angle; and each column represents a detector number, a detector distance, a detector angle, or a ray position; and a third sinogram dimension may optionally represent multiple detector rows.

151. The method according to claim 146 wherein the first sinogram data set is obtained from megavoltage CT images and the second sinogram data set is obtained from kilovoltage CT images.

152. The method according to claim 146 wherein the first sinogram data set is obtained from kilovoltage CT images and the second sinogram data set is obtained from megavoltage CT images.

153. The method according to claim 146 wherein the first sinogram data set is obtained from CT images and the second sinogram data set is obtained from MRI images.

154. The method according to claim 146 wherein the first sinogram data set is obtained from MRI images and the second sinogram data set is obtained from CT images.

155. The method according to claim 146 wherein the first sinogram data set is obtained from CT images and the second sinogram data set is obtained from PET images.

156. The method according to claim 146 wherein the first sinogram data set is obtained from PET images and the second sinogram data set is obtained from CT images.

157. The method according to claim 146 wherein the first sinogram data set is obtained from MRI images and the second sinogram data set is obtained from PET images.

158. The method according to claim 146 wherein the first sinogram data set is obtained from PET images and the second sinogram data set is obtained from MRI images.

159. The method according to claim 146 further comprising the step of completing one or more iterations by substituting the fusion-aligned reprojection image for the first image.

160. The method according to claim 146 wherein the first sinogram data set is obtained from a tomographic or volume-imaging modality.

161. The method according to claim 146 wherein the second sinogram data set is obtained from a tomographic or volume-imaging modality.

162. The method according to claim 146 wherein any of the sinograms or images are collected using fan-beam geometries.

163. The method according to claim 146 wherein any of the sinograms or images are collected using cone-beam geometries.

164. The method according to claim 146 wherein any of the sinograms or images are collected using helical geometries.

165. The method according to claim 146 wherein any of the sinograms or images are collected using planar image or data converted into tomographic-equivalent images or sinograms, or volume images.

166. The method according to claim 146 wherein the step of merging utilizes patient shape, size, or density information.

167. The method according to claim 146 wherein the patient's size, shape, and/or anatomy has changed between the collection of the first and second images or data sets.

168. A method of augmenting a tomographic projection image of a patient, the method comprising the steps of:
obtaining a first sinogram data set from a patient, the first sinogram data set including incomplete, imperfect or limited data;
obtaining a second sinogram data set from the patient using a different imaging apparatus or modality than the first sinogram data set, the second sinogram data set including complete data;
aligning the first sinogram data set to the second sinogram data set to obtain an aligned sinogram data set, so that optimal registration between the first and second sinogram data sets is obtained;
extracting data from the aligned sinogram data set that is missing from or not available in the first sinogram data set;
augmenting the first sinogram data set with the extracted data from the aligned sinogram data set to obtain an augmented sinogram data set; and
reconstructing the augmented sinogram data set into a fusion-aligned reprojection image.

169. The method according to claim 168 wherein the first sinogram data set is converted to an artifact-prone image.

170. The method according to claim 168 wherein the step of fusing comprises using common radiotherapy patient setup protocols.

171. The method according to claim 168 wherein the sinogram data sets are sufficiently well aligned that explicit fusion is not necessary.

172. The method according to claim 168 wherein the first sinogram data set, the aligned sinogram data set and the augmented sinogram data set are represented by a data matrix wherein each row represents a gantry position, a gantry angle, or a ray angle; and each column represents a detector number, a detector distance, a detector angle, or a ray position; and a third sinogram dimension may optionally represent multiple detector rows.

173. The method according to claim 168 wherein the first sinogram data set is obtained from megavoltage CT images and the second sinogram data set is obtained from kilovoltage CT images.

174. The method according to claim 168 wherein the first sinogram data set is obtained from kilovoltage CT images and the second sinogram data set is obtained from megavoltage CT images.

175. The method according to claim 168 wherein the first sinogram data set is obtained from CT images and the second sinogram data set is obtained from MRI images.

176. The method according to claim 168 wherein the first sinogram data set is obtained from MRI images and the second sinogram data set is obtained from CT images.

177. The method according to claim 168 wherein the first sinogram data set is obtained from CT images and the second sinogram data set is obtained from PET images.

178. The method according to claim 168 wherein the first sinogram data set is obtained from PET images and the second sinogram data set is obtained from CT images.

179. The method according to claim 168 wherein the first sinogram data set is obtained from MRI images and the second sinogram data set is obtained from PET images.

180. The method according to claim 168 wherein the first sinogram data set is obtained from PET images and the second sinogram data set is obtained from MRI images.

181. The method according to claim 168 further comprising the step of completing one or more iterations by substituting the augmented sinogram data set for the first sinogram data set.

182. The method according to claim 168 wherein the first sinogram data set is obtained from a tomographic or volume-imaging modality.

183. The method according to claim 168 wherein the second sinogram data set is obtained from a tomographic or volume-imaging modality.

184. The method according to claim 168 wherein any of the sinograms or images are collected using fan-beam geometries.

185. The method according to claim 168 wherein any of the sinograms or images are collected using cone-beam geometries.

186. The method according to claim 168 wherein any of the sinograms or images are collected using helical geometries.

187. The method according to claim 168 wherein any of the sinograms or images are collected using planar image or data converted into tomographic-equivalent images or sinograms, or volume images.

188. The method according to claim 168 wherein the step of merging utilizes patient shape, size, or density information.

189. The method according to claim 168 wherein the patient's size, shape, and/or anatomy has changed between the collection of the first and second data sets.

* * * * *